United States Patent
Owen et al.

(10) Patent No.: US 11,974,884 B2
(45) Date of Patent: May 7, 2024

(54) METHOD AND SYSTEM FOR DYNAMICALLY ADJUSTING IMAGING PARAMETERS DURING AN ULTRASOUND SCAN

(71) Applicant: GE Precision Healthcare LLC, Wauwatosa, WI (US)

(72) Inventors: Cynthia A. Owen, Powhatan, AR (US); Menachem Halmann, Monona, WI (US); Kjell Kristoffersen, Oslo (NO); Alexander Sokulin, Kiryat Tivon (IL)

(73) Assignee: GE Precision Healthcare LLC, Waukesha, WI (US)

( * ) Notice: Subject to any disclaimer, the term of this patent is extended or adjusted under 35 U.S.C. 154(b) by 0 days.

(21) Appl. No.: 17/526,145

(22) Filed: Nov. 15, 2021

(65) Prior Publication Data
US 2023/0148998 A1 May 18, 2023

(51) Int. Cl.
*A61B 8/08* (2006.01)
*A61B 8/00* (2006.01)

(52) U.S. Cl.
CPC .............. *A61B 8/5269* (2013.01); *A61B 8/54* (2013.01); *A61B 8/5207* (2013.01); *A61B 8/565* (2013.01)

(58) Field of Classification Search
CPC ................................ A61B 8/5269; A61B 8/54
See application file for complete search history.

(56) References Cited

U.S. PATENT DOCUMENTS

| 6,056,691 | A | 5/2000 | Urbano et al. | |
|---|---|---|---|---|
| 6,488,629 | B1 * | 12/2002 | Saetre | G16H 30/20 600/443 |
| 10,813,595 | B2 | 10/2020 | Tsymbalenko et al. | |
| 2009/0268953 | A1 * | 10/2009 | Crucs | A61B 6/583 382/128 |
| 2011/0077516 | A1 * | 3/2011 | Abe | A61B 8/0883 600/443 |
| 2011/0112401 | A1 * | 5/2011 | Watanaba | A61B 8/5207 600/443 |
| 2012/0065510 | A1 * | 3/2012 | Snare | G06T 7/75 600/443 |
| 2016/0143627 | A1 * | 5/2016 | Vignon | G06T 7/74 600/437 |

(Continued)

Primary Examiner — Joel Lamprecht
Assistant Examiner — Nyrobi Celestine
(74) Attorney, Agent, or Firm — McAndrews, Held & Malloy, Ltd.; Daniel Bissing; David Bates (57) ABSTRACT

A system and method for dynamically adjusting imaging parameters during an ultrasound scan is provided. The method includes acquiring regular ultrasound image frames based on a first set of imaging parameters and displaying the regular frames at a display system. The method includes intermittently acquiring a test ultrasound image frame based on a second set of imaging parameters having at least one imaging parameter that is different from the first set of imaging parameters. The test frame is not displayed. The method includes determining a regular frame image quality of at least one of the regular frames and a test frame image quality of the test frame. The method includes applying, in response to determining the test frame image quality exceeds the regular frame image quality, the second set of imaging parameters to acquire additional regular frames and displaying the additional regular frames at the display system.

20 Claims, 2 Drawing Sheets

(56) References Cited

U.S. PATENT DOCUMENTS

| | | | |
|---|---|---|---|
| 2016/0302759 A1* | 10/2016 | Shi | A61B 8/52 |
| 2017/0090571 A1* | 3/2017 | Bjaerum | A61B 8/4254 |
| 2018/0206820 A1* | 7/2018 | Anand | G01S 7/52085 |
| 2018/0214134 A1* | 8/2018 | Kim | A61B 8/4405 |
| 2018/0310920 A1* | 11/2018 | Specht | G09B 23/286 |
| 2019/0130554 A1* | 5/2019 | Rothberg | G06T 7/0002 |
| 2019/0142388 A1 | 5/2019 | Gonyeau et al. | |
| 2021/0068789 A1* | 3/2021 | Xu | A61B 8/461 |
| 2021/0128114 A1 | 5/2021 | Patil et al. | |

\* cited by examiner

METHOD AND SYSTEM FOR DYNAMICALLY ADJUSTING IMAGING PARAMETERS DURING AN ULTRASOUND SCAN

FIELD

Certain embodiments relate to ultrasound imaging. More specifically, certain embodiments relate to a method and system for dynamically adjusting imaging parameters during an ultrasound scan by intermittently acquiring a test ultrasound frame and comparing an image quality of the test ultrasound frame to an image quality of acquired regular ultrasound frames to determine optimal imaging parameters.

BACKGROUND

Ultrasound imaging is a medical imaging technique for imaging organs and soft tissues in a human body. Ultrasound imaging uses real time, non-invasive high frequency sound waves to produce a series of two-dimensional (2D) and/or three-dimensional (3D) images.

During an ultrasound imaging procedure, imaged tissue may have unexpected characteristics due to pathological states where a type of fluid is present, such as ascites, blood, cerebrospinal fluid, and the like. The different acoustic properties of types of fluid compared to tissue can cause imaging artifacts and decreased sound beam attenuation. In some cases, the fluid may distend the abdomen, or other anatomical structure, and increase scanning distances. For example, an abdomen of a patient with massive ascites or excessive amniotic fluid in pregnancy (e.g., polyhydramnios) may become enlarged due to the fluid; however, acoustic attenuation is much less compared to solid tissue. In such cases, there is no need to decrease frequency, which decreases spatial resolution; however, other imaging parameter adjustments may be performed to improve imaging quality and reduce the presence of artifacts, such as imaging parameter adjustments to the scan sequence, pulse repetition frequency (PRF), focus position, speckle reduction, time gain compensation (TGC), and/or any suitable imaging parameters. Ultrasound image artifacts caused by fluid, such as acoustic decay, multipath artifacts, reverberation artifacts, and posterior acoustic enhancement, may degrade image quality and obscure visualization of anatomy.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

A system and/or method is provided for dynamically adjusting imaging parameters during an ultrasound scan, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

DETAILED DESCRIPTION

Certain embodiments may be found in a method and system for dynamically adjusting imaging parameters during an ultrasound scan. Aspects of the present disclosure have the technical effect of acquiring regular ultrasound image frames based on a first set of imaging parameters, and intermittently acquiring a test ultrasound image frame based on a second set of imaging parameters. Various embodiments have the technical effect of determining an image quality of regular ultrasound image frames and determining an image quality of intermittently acquired test ultrasound image frames. Certain embodiments have the technical effect of dynamically switching to the second set of imaging parameters when the image quality of the test ultrasound image frame is greater than the image quality of the regular ultrasound image frames. Aspects of the present disclosure have the technical effect of presenting feedback at a display system regarding improved image parameter adjustments.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general-purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized, and that structural, logical and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and preceded with the word "a" or "an" should be understood as not excluding plural of said elements or steps, unless such exclusion is explicitly stated. Furthermore, references to "an exemplary embodiment," "various embodiments," "certain embodiments," "a representative embodiment," and the like are not intended to be interpreted as excluding the existence of additional embodiments that also incorporate the recited features. Moreover, unless explicitly stated to the contrary, embodiments "comprising", "including", or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode (2D mode), M-mode, three-dimensional (3D) mode, CF-mode, PW Doppler, CW Doppler, Contrast Enhanced Ultrasound (CEUS), and/or sub-modes of B-mode and/or CF such as Harmonic Imaging, Shear Wave Elasticity Imaging (SWEI), Strain Elastography, TVI, PDI, B-flow, MVI, UGAP, and in some cases also MM, CM, TVD where the "image" and/or "plane" includes a single beam or multiple beams.

Furthermore, the term processor or processing unit, as used herein, refers to any type of processing unit that can carry out the required calculations needed for the various embodiments, such as single or multi-core: CPU, Accelerated Processing Unit (APU), Graphic Processing Unit (GPU), DSP, FPGA, ASIC or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 1.

Figure 1:
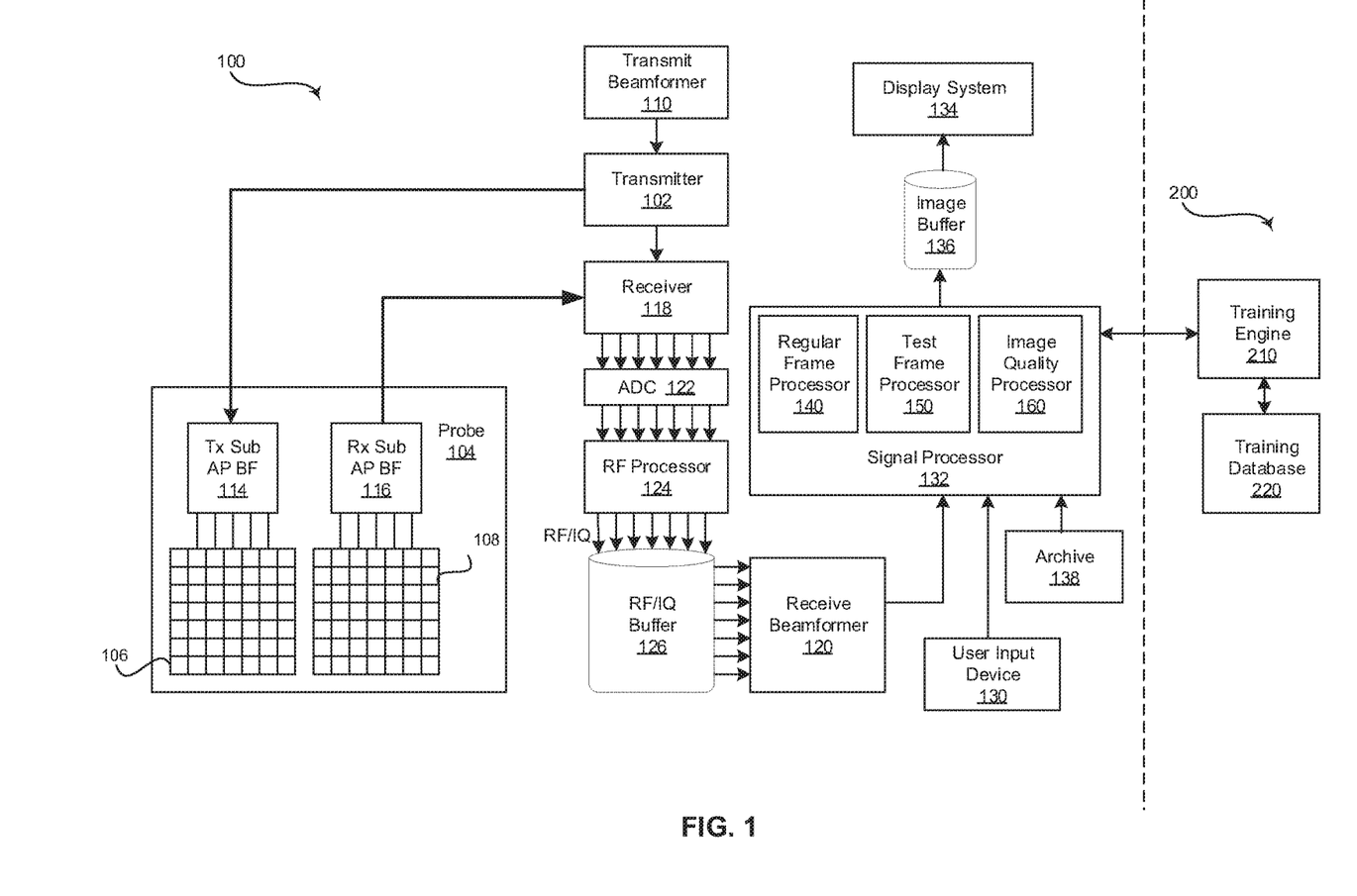
FIG. 1 is a block diagram of an exemplary ultrasound system that is operable to dynamically adjust imaging parameters during an ultrasound scan, in accordance with various embodiments.

FIG. 1 is a block diagram of an exemplary ultrasound system 100 that is operable to dynamically adjust imaging parameters during an ultrasound scan, in accordance with various embodiments. Referring to FIG. 1, there is shown an ultrasound system 100 and a training system 200. The ultrasound system 100 comprises a transmitter 102, an ultrasound probe 104, a transmit beamformer 110, a receiver 118, a receive beamformer 120, A/D converters 122, a RF processor 124, a RF/IQ buffer 126, a user input device 130, a signal processor 132, an image buffer 136, a display system 134, and an archive 138.

The transmitter 102 may comprise suitable logic, circuitry, interfaces and/or code that may be operable to drive an ultrasound probe 104. The ultrasound probe 104 may comprise a two dimensional (2D) array of piezoelectric elements. The ultrasound probe 104 may comprise a group of transmit transducer elements 106 and a group of receive transducer elements 108, that normally constitute the same elements. In certain embodiment, the ultrasound probe 104 may be operable to acquire ultrasound image data covering at least a substantial portion of an anatomy, such as the heart, a blood vessel, a fetus, or any suitable anatomical structure.

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 108.

The group of receive transducer elements 108 in the ultrasound probe 104 may be operable to convert the received echoes into analog signals, undergo sub-aperture beamforming by a receive sub-aperture beamformer 116 and are then communicated to a receiver 118. The receiver 118 may comprise suitable logic, circuitry, interfaces and/or code that may be operable to receive the signals from the receive sub-aperture beamformer 116. The analog signals may be communicated to one or more of the plurality of A/D converters 122.

The plurality of A/D converters 122 may comprise suitable logic, circuitry, interfaces and/or code that may be operable to convert the analog signals from the receiver 118 to corresponding digital signals. The plurality of A/D converters 122 are disposed between the receiver 118 and the RF processor 124. Notwithstanding, the disclosure is not limited in this regard. Accordingly, in some embodiments, the plurality of A/D converters 122 may be integrated within the receiver 118.

The RF processor 124 may comprise suitable logic, circuitry, interfaces and/or code that may be operable to demodulate the digital signals output by the plurality of A/D converters 122. In accordance with an embodiment, the RF processor 124 may comprise a complex demodulator (not shown) that is operable to demodulate the digital signals to form I/Q data pairs that are representative of the corresponding echo signals. The RF or I/Q signal data may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124.

The receive beamformer 120 may comprise suitable logic, circuitry, interfaces and/or code that may be operable to perform digital beamforming processing to, for example, sum the delayed channel signals received from RF processor 124 via the RF/IQ buffer 126 and output a beam summed signal. The resulting processed information may be the beam summed signal that is output from the receive beamformer 120 and communicated to the signal processor 132. In accordance with some embodiments, the receiver 118, the plurality of A/D converters 122, the RF processor 124, and the beamformer 120 may be integrated into a single beamformer, which may be digital. In various embodiments, the ultrasound system 100 comprises a plurality of receive beamformers 120.

The user input device 130 may be utilized to input patient data, regular frame image parameters, test frame image parameters, settings, select protocols and/or templates, accept recommended image parameters changes, and the like. In an exemplary embodiment, the user input device 130 may be operable to configure, manage and/or control operation of one or more components and/or modules in the ultrasound system 100. In this regard, the user input device 130 may be operable to configure, manage and/or control operation of the transmitter 102, the ultrasound probe 104, the transmit beamformer 110, the receiver 118, the receive beamformer 120, the RF processor 124, the RF/IQ buffer 126, the user input device 130, the signal processor 132, the image buffer 136, the display system 134, and/or the archive 138. The user input device 130 may include button(s), rotary encoder(s), a touchscreen, motion tracking, voice recognition, a mousing device, keyboard, camera and/or any other device capable of receiving a user directive. In certain embodiments, one or more of the user input devices 130 may be integrated into other components, such as the display system 134 or the ultrasound probe 104, for example. As an example, user input device 130 may include a touchscreen display.

The signal processor 132 may comprise suitable logic, circuitry, interfaces and/or code that may be operable to process ultrasound scan data (i.e., summed IQ signal) for generating regular ultrasound image frames acquired according to a first set of imaging parameters, and test ultrasound image frames acquired according to a second set of imaging parameters. The signal processor 132 may be configured to generate the regular ultrasound image frames for image quality analysis and presentation on a display system 134. The signal processor 132 may be configured to generate the test ultrasound image frames for image quality analysis. In various embodiments, the test ultrasound image frames may not be displayed. The signal processor 132 is operable to perform one or more processing operations according to a plurality of selectable ultrasound modalities on the acquired ultrasound scan data. In an exemplary embodiment, the signal processor 132 may be operable to perform display processing and/or control processing, among other things. Acquired ultrasound scan data may be processed in real-time during a scanning session as the echo signals are received. Additionally or alternatively, the ultrasound scan data may be stored temporarily in the RF/IQ buffer 126 during a scanning session and processed in less than real-time in a live or off-line operation. In various embodiments, the processed image data can be presented at the display system 134 and/or may be stored at the archive 138. The archive 138 may be a local archive, a Picture Archiving and Communication System (PACS), or any suitable device for storing images and related information.

The signal processor 132 may be one or more central processing units, microprocessors, microcontrollers, and/or the like. The signal processor 132 may be an integrated component, or may be distributed across various locations, for example. In an exemplary embodiment, the signal processor 132 may comprise a regular frame processor 140, a test frame processor 150, and an image quality processor 160. The signal processor 132 may be capable of receiving input information from a user input device 130 and/or archive 138, generating an output displayable by a display system 134, and manipulating the output in response to input information from a user input device 130, among other things. The signal processor 132, regular frame processor 140, test frame processor 150, and image quality processor 160 may be capable of executing any of the method(s) and/or set(s) of instructions discussed herein in accordance with the various embodiments, for example.

The ultrasound system 100 may be operable to continuously acquire ultrasound scan data at a frame rate that is suitable for the imaging situation in question. The continuously acquired ultrasound scan data may include regular ultrasound image frames and intermittently acquired test ultrasound image frames. For example, the ultrasound system 100 may acquire a test ultrasound image frame periodically between regular ultrasound image frames (e.g., every tenth frame, twentieth frame, or the like). The ultrasound system 100 may interleave acquisition of complete regular ultrasound image frames with complete test ultrasound image frames. Additionally and/or alternatively, the ultrasound system 100 may interleave regular frame transmission and test frame transmissions. Typical frame rates range from 20-120 but may be lower or higher. The acquired regular ultrasound image frames may be displayed on the display system 134 at a display-rate that can be the same as the frame rate, or slower or faster. In various embodiments, the acquired test ultrasound image frames are not displayed. An image buffer 136 is included for storing processed frames of acquired regular ultrasound scan data that are not scheduled to be displayed immediately. Preferably, the image buffer 136 is of sufficient capacity to store at least several minutes' worth of regular ultrasound image frames. The regular ultrasound image frames are stored in a manner to facilitate retrieval thereof according to its order or time of acquisition. The image buffer 136 may be embodied as any known data storage medium.

The signal processor 132 may include a regular frame processor 140 that comprises suitable logic, circuitry, interfaces and/or code that may be operable to receive and process regular ultrasound image frames for image quality analysis and presentation at the display system 134. The regular frame processor 140 may be configured to apply a first set of imaging parameters to acquire the regular ultrasound image frames. The first set of imaging parameters may comprise a pulse repetition frequency (PRF) (e.g., high or low PRF), harmonics on/off, a frequency (e.g., high, medium, or low), an aperture, a focus position, an acoustic power, speckle reduction, time gain compensation (TGC), and/or any suitable imaging parameter. The regular frame processor 140 may be configured to process the regular ultrasound image frames for presentation at the display system 134 and analysis by the image quality processor 160 as described below. The regular frame processor 140 may also store the regular ultrasound image frames at archive 138 and/or any suitable data storage medium.

The signal processor 132 may include test frame processor 150 that comprises suitable logic, circuitry, interfaces and/or code that may be operable to receive and process test ultrasound image frames for image quality analysis. The test frame processor 150 may be configured to apply a second set of imaging parameters to acquire the test ultrasound image frames. The test ultrasound image frames may be acquired intermittently, such as periodically after 10, 20, or any suitable number of regular ultrasound image frames have been acquired. In a representative embodiment, the test ultrasound image frames are not displayed. The second set of imaging parameters applied to acquire the test ultrasound image frames may have at least one imaging parameter that is different from the first set of imaging parameters applied to acquire the regular ultrasound image frames. For example, the second set of imaging parameters may include a high PRF parameter when the first set of imaging parameters include a low PRF parameter. As another example, the second set of imaging parameters may include a harmonics on parameter when the first set of imaging parameters include a harmonics off parameter. As another example, the second set of imaging parameters may include a medium or high frequency parameter when the first set of imaging parameters include a low frequency parameter. The different at least one parameter value may allow the image quality processor 160 to determine whether the second set of imaging parameters applied to acquire the test ultrasound image frame provide a higher image quality than the first set of imaging parameters applied to acquire the regular ultrasound image frames being presented at the display system 134, such that the image quality processor 160 may prompt a user and/or automatically update the first set of imaging parameters as described below. The test frame processor 150 may be configured to process the test ultrasound image frames for analysis by the image quality processor 160. The test frame processor 150 may also store the test ultrasound image frames at archive 138 and/or any suitable data storage medium.

In various embodiments, the test frame processor 150 may be configured to receive and process multiple test frames acquired concurrently. For example, the test frame processor 150 may be configured to apply a second set of imaging parameters to intermittently acquire a first test ultrasound image frame and a third set of imaging parameters to intermittently acquire a second test ultrasound image frame. As an example, the second set of imaging parameters may be optimized for improved resolution and the third set of imaging parameters may be optimized for improved penetration. The test frame processor 150 may be configured to process the first and second test ultrasound image frames for analysis by the image quality processor 160. The test frame processor 150 may also store the first and second test ultrasound image frames at archive 138 and/or any suitable data storage medium.

The signal processor 132 may include an image quality processor 160 that comprises suitable logic, circuitry, interfaces and/or code that may be operable to analyze and determine an image quality of the regular ultrasound image frames and at least one type of the test ultrasound image frame. The image quality processor 160 may include image analysis algorithms, artificial intelligence algorithms, one or more deep neural networks (e.g., a convolutional neural network) and/or may utilize any suitable form of image analysis techniques or machine learning processing functionality configured to determine an image quality of regular ultrasound image frames and test ultrasound image frames. In various embodiments, the image quality processor 160 may be configured to determine an image quality of the regular ultrasound image frames and the test ultrasound image frame(s) based on a presence or absence of artifacts, such as acoustic decay artifacts, multipath artifacts, reverberation artifacts, posterior acoustic enhancement artifacts, secondary echo artifacts, sidelobes, grating lobes, and/or any suitable image artifacts. Additionally and/or alternatively, the image quality processor 160 may be configured to determine an image quality of the regular ultrasound image frames and the test ultrasound image frame(s) based on an amount of image resolution and penetration, and/or any suitable image quality metric.

In certain embodiments, the image quality processor 160 may be provided as image analysis tools and/or algorithms configured to analyze histogram changes, variations to regular ultrasound image frames, and/or the like. Additionally and/or alternatively, the image quality processor 160 may be provided as a deep neural network that may be made up of, for example, an input layer, an output layer, and one or more hidden layers in between the input and output layers. Each of the layers may be made up of a plurality of processing nodes that may be referred to as neurons. For example, the image quality processor 160 may include an input layer having a neuron for each pixel or a group of pixels from a regular ultrasound image frame or test ultrasound image frame. The output layer may have a neuron corresponding to an image quality score. Each neuron of each layer may perform a processing function and pass the processed ultrasound image information to one of a plurality of neurons of a downstream layer for further processing. As an example, neurons of a first layer may learn to recognize edges of structure in the ultrasound image frame. The neurons of a second layer may learn to recognize shapes based on the detected edges from the first layer. The neurons of a third layer may learn positions of the recognized shapes relative to landmarks in the ultrasound image frame. The processing performed by the image quality processor 160 deep neural network (e.g., convolutional neural network) may assign an image quality score based on an image quality metric (e.g., presence of artifacts, amount of penetration/resolution, or the like) with a high degree of probability. In various embodiments, the image quality score can be provided for an entire frame. Additionally and/or alternatively, the frame may include multiple image quality scores for different portions of the frame. For example, portions of an image frame having artifacts may be scored lower than portions of an image frame without artifacts.

The image quality processor 160 may be configured to determine whether the image quality score associated with a regular ultrasound image frame is higher than the image quality score associated with the test ultrasound image frame(s). For example, the image quality processor 160 may compare an image quality score of the test ultrasound image frame(s) to an image quality score of the regular ultrasound image frame acquired immediately prior to the test ultrasound image frame(s). Additionally and/or alternatively, the image quality processor 160 may compare an image quality score of the test ultrasound image frame to an image quality score of the regular ultrasound image frame acquired immediately after the test ultrasound image frame(s). As another example, the image quality processor 160 may compare an image quality score of the test ultrasound image frame(s) to an average image quality score of the regular ultrasound image frames acquired prior to the test ultrasound image frame(s) (i.e., up until the previously acquired test ultrasound image frame(s)). The image quality processor 160 may be configured to maintain the first and second sets of imaging parameters and continue monitoring the image quality as the intermittent test ultrasound image frames are acquired when the regular ultrasound image frame image quality is greater than the test ultrasound image frame image quality. The image quality processor 160 may be configured to switch the first and second sets of imaging parameters and continue monitoring the image quality based on the switched first and second sets of imaging parameters when the regular ultrasound image frame image quality is less than the test ultrasound image frame image quality. For example, the image quality processor 160 may determine and analyze image quality of regular ultrasound image frames acquired with a high PRF and intermittent test ultrasound image frames acquired with a low PRF. The image quality processor 160 may change the regular ultrasound image frame acquisition to a low PRF and the intermittent test ultrasound image frame acquisition to a high PRF when the image quality processor 160 detects an acoustic artifact in the regular ultrasound image frames that is not present in the test ultrasound image frame, resulting in a lower image quality of the regular ultrasound image frames compared to the test ultrasound image frame. The image quality processor 160 continues monitoring the image quality and may switch back to regular ultrasound image frame acquisition with the high PRF when the acoustic artifact is no longer present in the test ultrasound image frame.

In various embodiments, the image quality processor 160 may factor frame rate or any suitable metric into the determining whether the image quality score associated with a regular ultrasound image frame is higher than the image quality score associated with the test ultrasound image frame. For example, regular and test ultrasound image frames that otherwise are assigned a same image quality score may be differentiated based on the frame rate. As an example, a test ultrasound image frame with a high frame rate may be determined to have an image quality exceeding an image quality of a regular ultrasound image frame with a low frame rate and an otherwise same image quality.

The image quality processor 160 may be configured to automatically switch first and second imaging parameter sets with no feedback, automatically switch with feedback, or may prompt a user to switch the first and second imaging parameters sets. For example, the image quality processor 160 may dynamically switch the first and second imaging parameter sets in response to the image quality analysis, without notifying a user of the change. As another example, the image quality processor 160 may dynamically switch the first and second imaging parameter sets in response to the image quality analysis, and may present an indication of the imaging parameter change at the display system 134. The indication of the imaging parameter change may be represented by an icon, textual message, or any suitable feedback. For example, the image quality processor 160 may present a textual message stating, "Longer decay time applied" when the first imaging parameter set is changed to the low PRF. In an exemplary embodiment, the image quality processor 160 may dynamically switch the first and second imaging parameter sets in response to the image quality analysis, and may present a split-screen display with the live regular ultrasound image frames having the new first set of imaging parameters and a now frozen last acquired regular ultrasound image frame having the old first set of imaging parameters. In various embodiments, the image quality processor 160 may provide an option switch back to the old first set of imaging parameters. In another exemplary embodiment, the image quality processor 160 may present a recommendation to switch the first and second sets of imaging parameters and provide a selectable option for accepting or declining the recommendation. In various embodiments, the automatic optimization of the first set of imaging parameters may be "on" as a default. Additionally and/or alternatively, the automatic optimization may be selectively turned "on" or "off" by a user interacting with the ultrasound system 100.

In certain embodiments, the image quality processor 160 may be configured to switch the first and second imaging parameter sets for only a portion of a frame. For example, if the image quality score for a first portion of the test ultrasound image frame is greater than an image quality score of a corresponding portion of the regular ultrasound image frame, but the image quality score for a second portion of the test ultrasound image frame is less than an image quality score of a corresponding portion of the regular ultrasound image frame, the image quality processor 160 may switch the first and second imaging parameter sets for acquisition of only the portion of the regular ultrasound image frames corresponding with the first portion of the test ultrasound image frame.

The display system 134 may be any device capable of communicating visual information to a user. For example, a display system 134 may include a liquid crystal display, a light emitting diode display, and/or any suitable display or displays. The display system 134 can be operable to present regular ultrasound image frames, feedback regarding imaging parameter changes, prompts to change imaging parameters to recommended imaging parameters, and/or any suitable information.

The archive 138 may be one or more computer-readable memories integrated with the ultrasound system 100 and/or communicatively coupled (e.g., over a network) to the ultrasound system 100, such as a Picture Archiving and Communication System (PACS), a server, a hard disk, floppy disk, CD, CD-ROM, DVD, compact storage, flash memory, random access memory, read-only memory, electrically erasable and programmable read-only memory and/or any suitable memory. The archive 138 may include databases, libraries, sets of information, or other storage accessed by and/or incorporated with the signal processor 132, for example. The archive 138 may be able to store data temporarily or permanently, for example. The archive 138 may be capable of storing medical image data, data generated by the signal processor 132, and/or instructions readable by the signal processor 132, among other things. In various embodiments, the archive 138 stores regular ultrasound image frames, test ultrasound image frames, sets of imaging parameters, instructions for determining an image quality of ultrasound image frames, instructions for switching sets of imaging parameters, and feedback instructions, for example.

Components of the ultrasound system 100 may be implemented in software, hardware, firmware, and/or the like. The various components of the ultrasound system 100 may be communicatively linked. Components of the ultrasound system 100 may be implemented separately and/or integrated in various forms. For example, the display system 134 and the user input device 130 may be integrated as a touchscreen display.

Still referring to FIG. 1, the training system 200 may comprise a training engine 210 and a training database 220. The training engine 210 may comprise suitable logic, circuitry, interfaces and/or code that may be operable to train the neurons of the deep neural network(s) (e.g., artificial intelligence model(s)) inferenced (i.e., deployed) by the image quality processor 160. For example, the artificial intelligence model inferenced by the image quality processor 160 may be trained to automatically identify artifacts, penetration, and/or resolution in ultrasound image frames. As an example, the training engine 210 may train the deep neural networks deployed by the image quality processor 160 using database(s) 220 of classified ultrasound image frames. The ultrasound image frames may include ultrasound image frames of a particular anatomical feature, including particular artifact types, or any suitable ultrasound image frames and features.

In various embodiments, the databases 220 of training images may be a Picture Archiving and Communication System (PACS), or any suitable data storage medium. In certain embodiments, the training engine 210 and/or training image databases 220 may be remote system(s) communicatively coupled via a wired or wireless connection to the ultrasound system 100 as shown in FIG. 1. Additionally and/or alternatively, components or all of the training system 200 may be integrated with the ultrasound system 100 in various forms.

Figure 2:
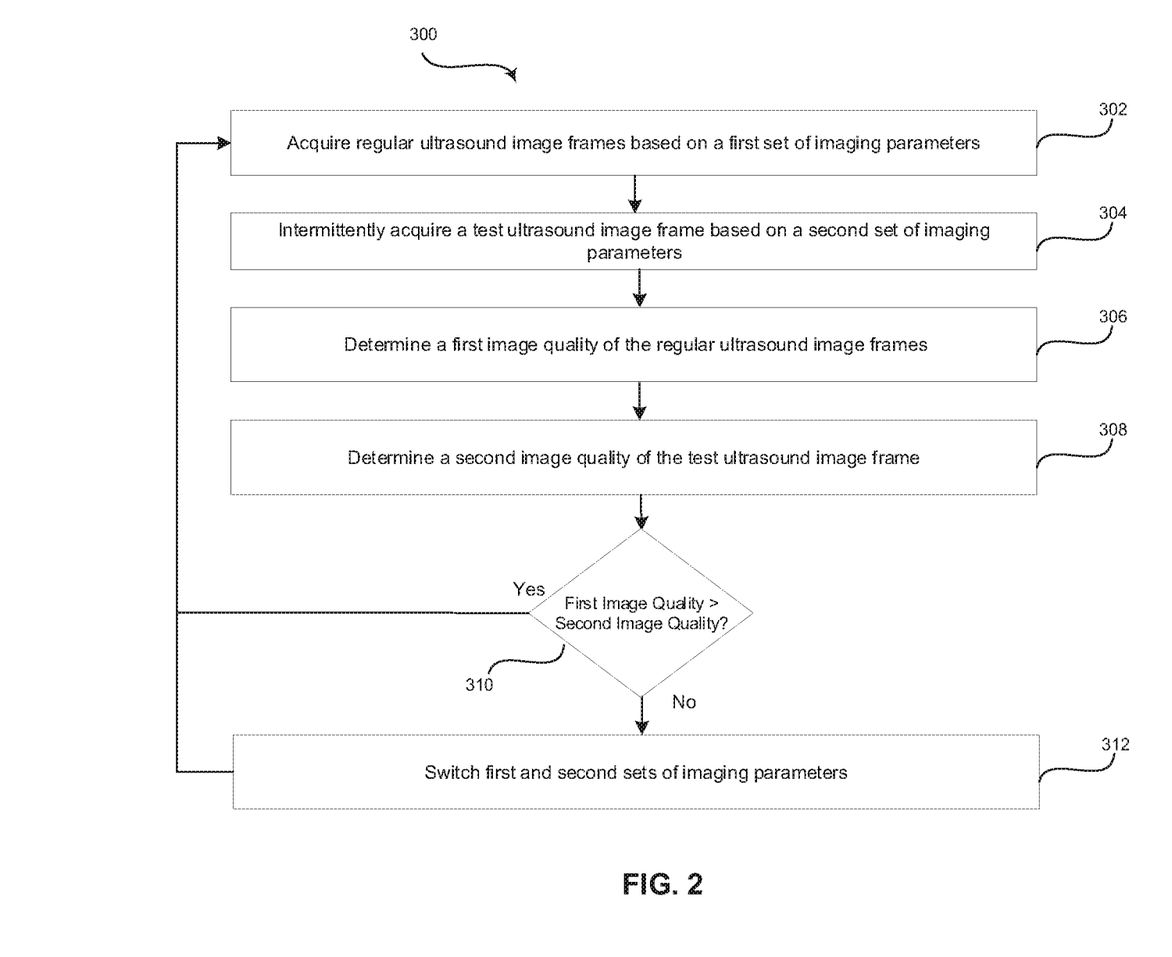
FIG. 2 is a flow chart illustrating exemplary steps that may be utilized for dynamically adjusting imaging parameters during an ultrasound scan, in accordance with various embodiments.

FIG. 2 is a flow chart 200 illustrating exemplary steps 302-312 that may be utilized for dynamically adjusting imaging parameters during an ultrasound scan, in accordance with various embodiments. Referring to FIG. 2, there is shown a flow chart 300 comprising exemplary steps 302 through 312. Certain embodiments may omit one or more of the steps, and/or perform the steps in a different order than the order listed, and/or combine certain of the steps discussed below. For example, some steps may not be performed in certain embodiments. As a further example, certain steps may be performed in a different temporal order, including simultaneously, than listed below.

At step 302, an ultrasound system 100 acquires regular ultrasound image frames based on a first set of imaging parameters. For example, the ultrasound system 100 may acquire, with an ultrasound probe 104 positioned at a scan position over an anatomical structure of interest, regular ultrasound image frames according to a first set of imaging parameters. A regular frame processor 140 of a signal processor 132 of the ultrasound system 100 may be configured to apply a first set of imaging parameters to acquire the regular ultrasound image frames. The first set of imaging parameters may comprise a pulse repetition frequency (PRF) (e.g., high or low PRF), harmonics on/off, a frequency (e.g., high, medium, or low), an aperture, a focus position, an acoustic power, speckle reduction, time gain compensation (TGC), and/or any suitable imaging parameter. The regular frame processor 140 may be configured to process the regular ultrasound image frames for presentation at the display system 134 and image quality analysis.

At step 304, the ultrasound system 100 intermittently acquires a test ultrasound image frame based on a second set of imaging parameters. For example, the ultrasound system 100 may periodically acquire, with an ultrasound probe 104 positioned at a scan position over the anatomical structure of interest, a test ultrasound image frame according to a second set of imaging parameters. As an example, the ultrasound system 100 may acquire the test ultrasound image frame every tenth, twentieth, or any suitable number of frames. The second set of imaging parameters applied to acquire the test ultrasound image frames may have at least one imaging parameter that is different from the first set of imaging parameters applied to acquire the regular ultrasound image frames. For example, the second set of imaging parameters may include a high PRF parameter when the first set of imaging parameters include a low PRF parameter. As another example, the second set of imaging parameters may include a harmonics on parameter when the first set of imaging parameters include a harmonics off parameter. As another example, the second set of imaging parameters may include a medium or high frequency parameter when the first set of imaging parameters include a low frequency parameter. A test frame processor 150 of the signal processor 132 of the ultrasound system 100 may be configured to process the test ultrasound image frames for image quality analysis. In various embodiments, the test ultrasound image frames are not displayed at the display system 134. In certain embodiments, the ultrasound system 100 may be configured to acquire multiple test frames concurrently. For example, the ultrasound system 100 may be configured to apply a second set of imaging parameters to intermittently acquire a first test ultrasound image frame and a third set of imaging parameters to intermittently acquire a second test ultrasound image frame. As an example, the second set of imaging parameters may be optimized for improved resolution and the third set of imaging parameters may be optimized for improved penetration.

At step 306, a signal processor 132 of the ultrasound system 100 may determine a first image quality of the regular ultrasound image frames. For example, the image quality processor 160 of the signal processor 132 may analyze the image quality of at least one of the regular ultrasound image frames. The image quality processor 160 may analyze the regular ultrasound image frame before or after the test ultrasound image frame. Additionally and/or alternatively, the image quality processor 160 may analyze a subset or all regular ultrasound image frames between test ultrasound image frames. The image quality processor 160 may include image analysis algorithms, artificial intelligence algorithms, one or more deep neural networks (e.g., a convolutional neural network) and/or may utilize any suitable form of image analysis techniques or machine learning processing functionality configured to determine an image quality of regular ultrasound image frames. In various embodiments, the image quality processor 160 may be configured to determine an image quality of the regular ultrasound image frames based on a presence or absence of artifacts, such as acoustic decay artifacts, multipath artifacts, reverberation artifacts, posterior acoustic enhancement artifacts, secondary echo artifacts, sidelobes, grating lobes, and/or any suitable image artifacts. Additionally and/or alternatively, the image quality processor 160 may be configured to determine an image quality of the regular ultrasound image frames based on an amount of image resolution and penetration, and/or any suitable image quality metric. In certain embodiments, the image quality processor 160 may be provided as image analysis tools and/or algorithms configured to provide an image quality score based on histogram changes, variations to a test ultrasound image frame, and/or the like. Additionally and/or alternatively, the image quality processor 160 may be provided as a deep neural network. The processing performed by the image quality processor 160 deep neural network (e.g., convolutional neural network) may assign an image quality score based on an image quality metric (e.g., presence of artifacts, amount of penetration/resolution, or the like). The image quality score can be provided for an entire frame and/or the frame may include multiple image quality scores for different portions of the frame.

At step 308, the signal processor 132 of the ultrasound system 100 may determine a second image quality of the test ultrasound image frame. For example, the image quality processor 160 of the signal processor 132 may be configured to determine an image quality of the test ultrasound image frame based on a presence or absence of artifacts, such as acoustic decay artifacts, multipath artifacts, reverberation artifacts, posterior acoustic enhancement artifacts, secondary echo artifacts, sidelobes, grating lobes, and/or any suitable image artifacts. Additionally and/or alternatively, the image quality processor 160 may be configured to determine an image quality of the test ultrasound image frames based on an amount of image resolution and penetration, and/or any suitable image quality metric. The image quality metric applied to assess the test ultrasound image frame is the same image quality metric applied to assess the regular ultrasound image frames. In certain embodiments, the image quality processor 160 may be provided as image analysis tools and/or algorithms configured to provide an image quality score based on histogram changes, variations to a regular ultrasound image frame, and/or the like. Additionally and/or alternatively, the image quality processor 160 may be provided as a deep neural network. The processing performed by the image quality processor 160 deep neural network (e.g., convolutional neural network) may assign an image quality score based on an image quality metric (e.g., presence of artifacts, amount of penetration/resolution, or the like). The image quality score can be provided for an entire frame and/or the frame may include multiple image quality scores for different portions of the frame. In various embodiments, the image quality processor 160 may be configured to determine a third image quality of a second type of test ultrasound image frame in embodiments where multiple test ultrasound image frame types are acquired at step 304.

At step 310, the signal processor 132 of the ultrasound system 100 may determine whether the first image quality of the regular ultrasound image frames is greater than the second image quality of the test ultrasound image frame. For example, the image quality processor 160 of the signal processor 132 may be configured to determine whether the image quality score associated with a regular ultrasound image frame is higher than the image quality score associated with the test ultrasound image frame. For example, the image quality processor 160 may compare an image quality score of the test ultrasound image frame to an image quality score of the regular ultrasound image frame (or an average image quality score of multiple regular ultrasound image frames). The image quality processor 160 may factor frame rate or any suitable metric into the determining whether the image quality score associated with a regular ultrasound image frame is higher than the image quality score associated with the test ultrasound image frame. The process 300 may return to step 302 to maintain the first and second sets of imaging parameters and continue monitoring the image quality as the intermittent test ultrasound image frames are acquired when the regular ultrasound image frame image quality is greater than the test ultrasound image frame image quality. The process 300 may proceed to step 312 when the regular ultrasound image frame image quality is less than the test ultrasound image frame image quality. In various embodiments, the image quality processor 160 may be configured to determine whether the first image quality of the regular ultrasound image frames is greater than a third image quality of a second type of test ultrasound image frame in embodiments where multiple test ultrasound image frame types are acquired at step 304 with the image quality determined at step 308.

At step 312, the signal processor 132 of the ultrasound system 100 may switch the first and second sets of imaging parameters. For example, the image quality processor 160 of the signal processor 132 may be configured to switch the first and second sets of imaging parameters and continue monitoring the image quality based on the switched first and second sets of imaging parameters when the image quality processor 160 determines that the regular ultrasound image frame image quality is less than the test ultrasound image frame image quality at step 310. For example, the image quality processor 160 may change the regular ultrasound image frame acquisition from a high PRF to a low PRF, and the intermittent test ultrasound image frame acquisition from a low PRF to a high PRF when the image quality processor 160 detects a lower image quality of the regular ultrasound image frames compared to the test ultrasound image frame (e.g., due to a presence of an acoustic artifact). As another example, the image quality processor 160 may change the regular ultrasound image frame acquisition from a low frequency to a medium or high frequency, and the intermittent test ultrasound image frame acquisition from a high or medium frequency to a low frequency when the image quality processor 160 detects a lower image quality of the regular ultrasound image frames compared to the test ultrasound image frame (e.g., due to a better combination of image resolution and penetration in the test ultrasound image frame). The switch from the first set of imaging parameters to the second set of imaging parameters may be automatic with no feedback, automatic with feedback, in response to a user selection based on a displayed recommendation with a user selection prompt, or the like. The process 300 may return to step 302 to continue monitoring the image quality of regular and test ultrasound image frames until the ultrasound examination is complete. In various embodiments, the image quality processor 160 may be configured to switch the first and third sets of imaging parameters and continue monitoring the image quality based on the switched first and third sets of imaging parameters when the image quality processor determines that the first image quality of the regular ultrasound image frames is less than a third image quality of a second type of test ultrasound image frame in embodiments where multiple test ultrasound image frame types are acquired at step 304 with the image quality determined at step 308.

Aspects of the present disclosure provide a method 300 and system 100 for dynamically adjusting imaging parameters during an ultrasound scan. In accordance with various embodiments, the method 300 may comprise acquiring 302, by an ultrasound system 100, regular ultrasound image frames based on a first set of imaging parameters and displaying the regular ultrasound image frames at a display system 134 of the ultrasound system 100. The method 300 may comprise intermittently acquiring 304, by the ultrasound system 100, a test ultrasound image frame based on a second set of imaging parameters. At least one of the second set of imaging parameters is different from the first set of imaging parameters. The test ultrasound image is not displayed at the display system 134. The method 300 may comprise determining 306, 308, by at least one processor 132, 160 of the ultrasound system 100, a regular frame image quality of at least one of the regular ultrasound image frames and a test frame image quality of the test ultrasound image frame. The method 300 may comprise applying 312, 302, by the at least one processor 132, 140, 160 and in response to determining 310 the test frame image quality exceeds the regular frame image quality, the second set of imaging parameters to acquire additional regular ultrasound image frames and displaying the additional regular ultrasound image frames at the display system 134.

In a representative embodiment, the method 300 may comprise applying 312, 304, by the at least one processor 132, 150, 160 and in response to the determining the test frame image quality exceeds the regular frame image quality, the first set of imaging parameters to intermittently acquire an additional test ultrasound image frame. In an exemplary embodiment, the regular frame image quality and the test frame image quality is based on a presence or absence of at least one artifact detected by the at least one processor 132, 160 in the at least one of the regular ultrasound image frames and the test ultrasound image frame. The at least one artifact may comprise at least one of an acoustic decay artifact, a multipath artifact, a reverberation artifact, a posterior acoustic enhancement artifact, a secondary echo artifact, sidelobes, or grating lobes. In various embodiments, the regular frame image quality and the test frame image quality is based on an amount of resolution and penetration in the at least one of the regular ultrasound image frames and the test ultrasound image frame. In certain embodiments, the at least one of the second set of imaging parameters that is different from the first set of imaging parameters is one of different pulse repetition frequencies, harmonics on or off, frequencies, aperture sizes, focus positions, or acoustic power amounts. In a representative embodiment, the applying 312, 302 the second set of imaging parameters in response to determining the test frame image quality exceeds the regular frame image quality is performed one of automatically and without displaying a notification of changed imaging parameters, or automatically and with the notification of changed imaging parameters presented at the display system 134. In an exemplary embodiment, the method 300 may comprise intermittently acquiring 304, by the ultrasound system 100, a second test ultrasound image frame based on a third set of imaging parameters. At least one of the third set of imaging parameters is different from the first set of imaging parameters. The second test ultrasound image is not displayed at the display system 134. The method 300 may comprise determining 308, by the at least one processor, a second test frame image quality of the second test ultrasound image frame. The method 300 may comprise applying 312, 302, by the at least one processor 132, 140, 160 and in response to determining the second test frame image quality exceeds the regular frame image quality, the third set of imaging parameters to acquire the additional regular ultrasound image frames and displaying the additional regular ultrasound image frames at the display system 134. In certain embodiments, the method 300 may comprise displaying 312, 302 a last of the regular ultrasound image frames acquired based on the first set of imaging parameters with the additional regular ultrasound image frames acquired based on the second set of imaging parameters, and displaying a selectable option to switch back the first set of imaging parameters.

Various embodiments provide a system 100 for dynamically adjusting imaging parameters during an ultrasound scan. The system may comprise an ultrasound system 100, at least one processor 132, 140, 150, 160, and a display system 134. The ultrasound system 100 may be configured to acquire regular ultrasound image frames based on a first set of imaging parameters. The ultrasound system 100 may be configured to intermittently acquire a test ultrasound image frame based on a second set of imaging parameters. At least one of the second set of imaging parameters is different from the first set of imaging parameters. The test ultrasound image is not displayed. The ultrasound system 100 may be configured to acquire additional regular ultrasound image frames based on the second set of imaging parameters. The at least one processor 132, 160 may be configured to determine a regular frame image quality of at least one of the regular ultrasound image frames and a test frame image quality of the test ultrasound image frame. The at least one processor 132, 140, 160 may be configured to apply, in response to determining the test frame image quality exceeds the regular frame image quality, the second set of imaging parameters to acquire the additional regular ultrasound image frames based on the second set of imaging parameters. The display system 134 may be configured to present the regular ultrasound image frames and the additional regular ultrasound image frames.

In an exemplary embodiment, the at least one processor 132, 150, 160 is configured to apply, in response to the determining the test frame image quality exceeds the regular frame image quality, the first set of imaging parameters to intermittently acquire an additional test ultrasound image frame. In various embodiments, the regular frame image quality and the test frame image quality is based on a presence or absence of at least one artifact detected in the at least one processor 132, 160 in the at least one of the regular ultrasound image frames and the test ultrasound image frame. The at least one artifact may comprise at least one of an acoustic decay artifact, a multipath artifact, a reverberation artifact, a posterior acoustic enhancement artifact, a secondary echo artifact, sidelobes, or grating lobes. In certain embodiments, the regular frame image quality and the test frame image quality is based on an amount of resolution and penetration in the at least one of the regular ultrasound image frames and the test ultrasound image frame. In a representative embodiment, the at least one of the second set of imaging parameters that is different from the first set of imaging parameters is one of different pulse repetition frequencies, harmonics on or off, frequencies, aperture sizes, focus positions, or acoustic power amounts. In an exemplary embodiment, the at least one processor 132, 140, 160 may be configured to apply the second set of imaging parameters in response to determining the test frame image quality exceeds the regular frame image quality automatically and without causing the display system 134 to present a notification of changed imaging parameters. The at least one processor 132, 140, 160 may be configured to apply the second set of imaging parameters in response to determining the test frame image quality exceeds the regular frame image quality automatically and with the notification of changed imaging parameters presented at the display system 134. In various embodiments, the display system 134 may be configured to present a last of the regular ultrasound image frames acquired based on the first set of imaging parameters with the additional regular ultrasound image frames acquired based on the second set of imaging parameters, and a selectable option to switch back the first set of imaging parameters.

Certain embodiments provide a non-transitory computer readable medium having stored thereon, a computer program having at least one code section. The at least one code section is executable by a machine for causing an ultrasound system to perform steps 300. The steps 300 may comprise receiving 302 regular ultrasound image frames acquired based on a first set of imaging parameters and displaying the regular ultrasound image frames at a display system 134 of the ultrasound system 100. The steps 300 may comprise receiving 302 a test ultrasound image frame intermittently acquired based on a second set of imaging parameters. At least one of the second set of imaging parameters is different from the first set of imaging parameters. The test ultrasound image is not displayed at the display system 134. The steps 300 may comprise determining 306, 308 a regular frame image quality of at least one of the regular ultrasound image frames and a test frame image quality of the test ultrasound image frame. The steps 300 may comprise applying 312, 302, in response to determining 310 the test frame image quality exceeds the regular frame image quality, the second set of imaging parameters to acquire additional regular ultrasound image frames and displaying the additional regular ultrasound image frames at the display system 134.

In various embodiments, the steps 300 may comprise applying 312, 304, in response to the determining 310 the test frame image quality exceeds the regular frame image quality, the first set of imaging parameters to intermittently acquire an additional test ultrasound image frame. In a representative embodiment, the regular frame image quality and the test frame image quality is based on a presence or absence of at least one artifact detected in the at least one of the regular ultrasound image frames and the test ultrasound image frame. The at least one artifact may comprise at least one of an acoustic decay artifact, a multipath artifact, a reverberation artifact, a posterior acoustic enhancement artifact, a secondary echo artifact, sidelobes, or grating lobes. In an exemplary embodiment, the regular frame image quality and the test frame image quality is based on an amount of resolution and penetration in the at least one of the regular ultrasound image frames and the test ultrasound image frame. In certain embodiments, the applying 312, 302 the second set of imaging parameters in response to determining 310 the test frame image quality exceeds the regular frame image quality is performed one of automatically and without displaying a notification of changed imaging parameters, or automatically and with the notification of changed imaging parameters presented at the display system 134.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. As another example, "x, y, and/or z" means any element of the seven-element set {(x), (y), (z), (x, y), (x, z), (y, z), (x, y, z)}. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" and/or "configured" to perform a function whenever the circuitry comprises the necessary hardware and code (if any is necessary) to perform the function, regardless of whether performance of the function is disabled, or not enabled, by some user-configurable setting.

Other embodiments may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for dynamically adjusting imaging parameters during an ultrasound scan.

Accordingly, the present disclosure may be realized in hardware, software, or a combination of hardware and software. The present disclosure may be realized in a centralized fashion in at least one computer system, or in a distributed fashion where different elements are spread across several interconnected computer systems. Any kind of computer system or other apparatus adapted for carrying out the methods described herein is suited.

Various embodiments may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What is claimed is:

1. A method comprising:
    acquiring, by an ultrasound system, regular ultrasound image frames based on a first set of imaging parameters and displaying the regular ultrasound image frames at a display system of the ultrasound system;
    periodically acquiring in an interleaved manner, by the ultrasound system, a test ultrasound image frame based on a second set of imaging parameters, wherein at least one of the second set of imaging parameters is different from the first set of imaging parameters, and wherein the test ultrasound image is not displayed at the display system;
    determining, by at least one processor of the ultrasound system, a regular frame image quality of at least one of the regular ultrasound image frames and a test frame image quality of the test ultrasound image frame; and
    applying, by the at least one processor and in response to determining the test frame image quality exceeds the regular frame image quality, the second set of imaging parameters to acquire additional regular ultrasound image frames and displaying the additional regular ultrasound image frames at the display system.

2. The method of claim 1, comprising applying, by the at least one processor and in response to the determining the test frame image quality exceeds the regular frame image quality, the first set of imaging parameters to periodically acquire an additional test ultrasound image frame.

3. The method of claim 1, wherein the regular frame image quality and the test frame image quality is based on a presence or absence of at least one artifact detected by the at least one processor in the at least one of the regular ultrasound image frames and the test ultrasound image frame, and wherein the at least one artifact comprises at least one of:
    an acoustic decay artifact,
    a multipath artifact,
    a reverberation artifact,
    a posterior acoustic enhancement artifact,
    a secondary echo artifact,
    sidelobes, or
    grating lobes.

4. The method of claim 1, wherein the regular frame image quality and the test frame image quality is based on an amount of resolution and penetration in the at least one of the regular ultrasound image frames and the test ultrasound image frame.

5. The method of claim 1, wherein the at least one of the second set of imaging parameters that is different from the first set of imaging parameters is one of different:
    pulse repetition frequencies,
    harmonics on or off,
    frequencies,
    aperture sizes,
    focus positions, or
    acoustic power amounts.

6. The method of claim 1, wherein the applying the second set of imaging parameters in response to determining the test frame image quality exceeds the regular frame image quality is performed one of:
    automatically and without displaying a notification of changed imaging parameters, or
    automatically and with the notification of changed imaging parameters presented at the display system.

7. The method of claim 1, comprising:
    periodically acquiring, by the ultrasound system, a second test ultrasound image frame based on a third set of imaging parameters, wherein at least one of the third set of imaging parameters is different from the first set of imaging parameters, and wherein the second test ultrasound image is not displayed at the display system;
    determining, by the at least one processor, a second test frame image quality of the second test ultrasound image frame; and
    applying, by the at least one processor and in response to determining the second test frame image quality exceeds the regular frame image quality, the third set of imaging parameters to acquire additional regular ultrasound image frames and displaying the additional regular ultrasound image frames at the display system.

8. The method of claim 1, comprising:
    displaying a last of the regular ultrasound image frames acquired based on the first set of imaging parameters with the additional regular ultrasound image frames acquired based on the second set of imaging parameters, and
    displaying a selectable option to switch back to the first set of imaging parameters.

9. A system comprising:
    an ultrasound system configured to:
        acquire regular ultrasound image frames based on a first set of imaging parameters;
        periodically acquire, in an interleaved manner, a test ultrasound image frame based on a second set of imaging parameters, wherein at least one of the second set of imaging parameters is different from the first set of imaging parameters, and wherein the test ultrasound image is not displayed; and
        acquire additional regular ultrasound image frames based on the second set of imaging parameters;
    at least one processor configured to:
        determine a regular frame image quality of at least one of the regular ultrasound image frames and a test frame image quality of the test ultrasound image frame; and
        apply, in response to determining the test frame image quality exceeds the regular frame image quality, the second set of imaging parameters to acquire the additional regular ultrasound image frames based on the second set of imaging parameters; and
    a display system configured to present the regular ultrasound image frames and the additional regular ultrasound image frames.

10. The system of claim 9, wherein the at least one processor is configured to apply, in response to the determining the test frame image quality exceeds the regular frame image quality, the first set of imaging parameters to periodically acquire an additional test ultrasound image frame.

11. The system of claim 9, wherein the regular frame image quality and the test frame image quality is based on a presence or absence of at least one artifact detected by the at least one processor in the at least one of the regular ultrasound image frames and the test ultrasound image frame, and wherein the at least one artifact comprises at least one of:
    an acoustic decay artifact,
    a multipath artifact,
    a reverberation artifact,
    a posterior acoustic enhancement artifact,
    a secondary echo artifact,
    sidelobes, or
    grating lobes.

12. The system of claim 9, wherein the regular frame image quality and the test frame image quality is based on an amount of resolution and penetration in the at least one of the regular ultrasound image frames and the test ultrasound image frame.

13. The system of claim 9, wherein the at least one of the second set of imaging parameters that is different from the first set of imaging parameters is one of different:
    pulse repetition frequencies,
    harmonics on or off,
    frequencies,
    aperture sizes,
    focus positions, or
    acoustic power amounts.

14. The system of claim 9, wherein the at least one processor is configured to apply the second set of imaging parameters in response to determining the test frame image quality exceeds the regular frame image quality one of:
    automatically and without causing the display system to present a notification of changed imaging parameters, or
    automatically and with the notification of changed imaging parameters presented at the display system.

15. The system of claim 9, wherein the display system is configured to present:
    a last of the regular ultrasound image frames acquired based on the first set of imaging parameters with the additional regular ultrasound image frames acquired based on the second set of imaging parameters, and
    a selectable option to switch back to the first set of imaging parameters.

16. A non-transitory computer readable medium having stored thereon, a computer program having at least one code section, the at least one code section being executable by a machine for causing an ultrasound system to perform steps comprising:
    receiving regular ultrasound image frames acquired based on a first set of imaging parameters and displaying the regular ultrasound image frames at a display system of the ultrasound system;
    receiving a test ultrasound image frame periodically acquired in an interleaved manner based on a second set of imaging parameters, wherein at least one of the second set of imaging parameters is different from the first set of imaging parameters, and wherein the test ultrasound image is not displayed at the display system;
    determining a regular frame image quality of at least one of the regular ultrasound image frames and a test frame image quality of the test ultrasound image frame; and
    applying, in response to determining the test frame image quality exceeds the regular frame image quality, the second set of imaging parameters to acquire additional regular ultrasound image frames and displaying the additional regular ultrasound image frames at the display system.

17. The non-transitory computer readable medium of claim 16, comprising applying, in response to the determining the test frame image quality exceeds the regular frame image quality, the first set of imaging parameters to periodically acquire an additional test ultrasound image frame.

18. The non-transitory computer readable medium of claim 16, wherein the regular frame image quality and the test frame image quality is based on a presence or absence of at least one artifact detected in the at least one of the regular ultrasound image frames and the test ultrasound image frame, and wherein the at least one artifact comprises at least one of:
    an acoustic decay artifact,
    a multipath artifact,
    a reverberation artifact,
    a posterior acoustic enhancement artifact,
    a secondary echo artifact,
    sidelobes, or
    grating lobes.

19. The non-transitory computer readable medium of claim 16, wherein the regular frame image quality and the test frame image quality is based on an amount of resolution and penetration in the at least one of the regular ultrasound image frames and the test ultrasound image frame.

20. The non-transitory computer readable medium of claim 16, wherein the applying the second set of imaging parameters in response to determining the test frame image quality exceeds the regular frame image quality is performed one of:
  automatically and without displaying a notification of changed imaging parameters, or
  automatically and with the notification of changed imaging parameters presented at the display system.

* * * * *